(12) United States Patent
Drinovec et al.

(10) Patent No.: US 11,566,991 B2
(45) Date of Patent: Jan. 31, 2023

(54) METHOD FOR QUANTIFICATION OF MINERAL DUST IN AIR BASED ON OPTICAL ABSORPTION OF PARTICLES CONCENTRATED BY A VIRTUAL IMPACTOR AND A DEVICE PERFORMING THE SAID METHOD

(71) Applicant: AEROSOL D.O.O., Ljubljana (SI)

(72) Inventors: Luka Drinovec, Ljubljana (SI); Grisa Mocnik, Ljubljana (SI); Iasonas Stavroulas, Athens (GR); Spiros Bezantakos, Nicosia (CY); Michael Pikridas, Pireaus (GR); Florin Unga, Nicosia (CY); Jean Sciare, Aglantzia Nicosia (CY)

( * ) Notice: Subject to any disclaimer, the term of this patent is extended or adjusted under 35 U.S.C. 154(b) by 82 days.

(21) Appl. No.: 16/999,874

(22) Filed: Aug. 21, 2020

(65) Prior Publication Data
US 2021/0055198 A1 Feb. 25, 2021

(30) Foreign Application Priority Data
Aug. 23, 2019 (EP) ..................................... 19193244

(51) Int. Cl.
*G01N 15/06* (2006.01)
*G01N 33/00* (2006.01)
*G01N 15/02* (2006.01)

(52) U.S. Cl.
CPC ......... *G01N 15/06* (2013.01); *G01N 33/0004* (2013.01); *G01N 2015/0261* (2013.01)

(58) Field of Classification Search
CPC ............... G01N 15/06; G01N 33/0004; G01N 2015/0261
See application file for complete search history.

(56) References Cited

U.S. PATENT DOCUMENTS

| | | | |
|---|---|---|---|
| 6,594,001 B1 | 7/2003 | Yabusaki | |
| 2013/0042893 A1 | 2/2013 | Ariessohn | |
| 2014/0053629 A1 | 2/2014 | Cahill | |
| 2018/0328889 A1* | 11/2018 | Hansen | ..................... G01N 5/02 |
| 2019/0358387 A1* | 11/2019 | Elbadry | .............. A61M 1/3663 |

OTHER PUBLICATIONS

European Search Report for EP19193244.1.
Viana et al. (2010; https://doi.org/10.1021/es1022625).
Ganor et al, 2009; https://doi.org/10.1016/j.atmosenv.2009.07.028.

* cited by examiner

*Primary Examiner* — David Z Huang
(74) *Attorney, Agent, or Firm* — Voyer Law

(57) ABSTRACT

The invention relates to a method for determination of ambient mineral dust concentration based on optical absorption of particles concentrated by a virtual impactor as well as a device performing the said method. The method comprises the following steps:

Sampling air samples with particle size smaller than 1 μm ($PM_1$) and sampling air samples with particle size up to 10 μm;

Concentrating the samples with particle sizes up to 10 μm with a virtual impactor;

Measuring optical absorption of collected samples at least one wavelength from UV to IR spectre, preferably from 370 to 950 nm, most preferably at 370 nm;

Subtracting the absorption of the samples with particle size smaller than 1 μm from the absorption of the sample concentrated by the virtual impactor.

12 Claims, No Drawings

METHOD FOR QUANTIFICATION OF MINERAL DUST IN AIR BASED ON OPTICAL ABSORPTION OF PARTICLES CONCENTRATED BY A VIRTUAL IMPACTOR AND A DEVICE PERFORMING THE SAID METHOD

FIELD OF THE INVENTION

The present invention belongs to the field of devices and methods for measurement of particle concentration, more precisely to the field of devices and methods for quantification of particles based on their physical characteristics, especially using optical means. The invention relates to a method for determination of mineral dust concentration in air based on optical absorption of particles concentrated by a virtual impactor as well as a device performing the said method.

Background of the Invention and the Technical Problem

Mineral dust is an expression covering particles in air, which originate from the suspension of minerals constituting the soil. It is mainly composed of various oxides and carbonates, while the exact elemental composition depends on the source of the dust. The Sahara Desert is believed to be the major source of mineral dust that spreads across the Mediterranean to Europe and also across the Caribbean seas into northern South America, Central America, and eastern North America. Another source of airborne mineral dust is the Gobi Desert affecting eastern Asia and western North America.

Dust particles found in air have effects on several different aspects, most importantly on the climate, on biogeochemistry of various ecosystems and human health. As reported by Middleton et al. (2008, doi: 10.1168/1476-069X-7-39) and Perez et al. (2012, doi: 10.1016/j.envint2012.07.001) Saharan dust events were shown to increase morbidity mainly through respiratory and cardiovascular effects. Further, several studies suggest that mineral dust spread from deserts plays a significant role in the nutrient inflow to other ecosystems, such as the Amazon rainforest (Koren et al., 2006; doi:10.1088/1748-9326/1/1/014005). Iron is an essential element for all biological organisms including those in marine environments. Oceans are a well-known environment with scarce iron availability, however mineral dust aerosol, mainly desert dust and dust from volcanic eruptions, is a source of iron and can thus increase the amount of biologically available iron in parts where dust deposits are common.

Even more importantly, optical properties of mineral dust significantly differ from properties of atmospheric gases. Dust particles can absorb and scatter solar radiation, which affects the Earth's radiation balance, consequently resulting in regional climate and precipitation changes. Mineral dust can interact with clouds as it functions as cloud nucleation nuclei. Thus, the size distribution, residence time, and optical properties of the clouds is affected, possibly causing unexpected climate changes. In addition, mineral dust deposited onto snow and sea ice can reduce albedo of snow that may alter the timing of snow melt.

Due to its significant effects airborne mineral dust is followed daily, however the currently known methods are not satisfactorily quantitative. There is a need for a reliable, real-time method for determination of dust concentration in the atmosphere, which could also contribute to improved understanding of the nature, transport and removal of mineral dust.

According to European Air Quality Directive (2008/50/EC) mineral dust is natural aerosol and can be used for correction of days on which the $PM_{10}$ value was exceeded as discussed in Viana et al. (2010; https://doi.org/10.1021/es1022625). Such corrections lead to lower penalties for exceeding $PM_{10}$ values. Thus, it is important to reliably quantify mineral dust in air, while it is desired to retain the simplicity of one-parameter measurements.

To sum up, the technical problem solved by the present invention is design of a method for real-time quantification of mineral dust in air.

STATE OF THE ART

One of the widely used methods to determine mineral dust in air is the 24-hour filter method, wherein air samples are collected on suitable filters for 24 hours, after which the filters are taken for analysis of chemical composition, especially of calcium as desert dust comprises oxides such as $SiO_2$, $AlO_3$, $FeO$, $Fe_2O_3$, and $CaO$, as well as carbonates such as $CaCO_3$ and $MgCO_3$ that constitute the Earth's crust. Phosphorus and lead may also be found in dust particles. This method only shows results for individual days and does not allow specific time mapping of dust peaks during one day. Further, the samples need to be collected and analysed, which takes time and thus increases the costs of the method.

Several different aerosol parameters can be determined based on measurements of scattering and absorption with known devices, such as single scattering albedo (SSA), absorption Angstrom exponent (AAE), and single scattering albedo Angstrom exponent (SSAAE), however, these parameters are only qualitative and not quantitative. Single-scattering albedo is the ratio of scattering efficiency to total extinction efficiency (a sum of scattering and absorption). It is unit-less, and a value of unity implies that all particle extinction is due to scattering; conversely, a single-scattering albedo of zero implies that all extinction is due to absorption. AAE is a parameter that describes how the optical thickness of an aerosol typically depends on the wavelength of the light. By combining absorption and scattering measurements, it is possible to identify the mineral dust events as the periods during which the single scattering albedo Angstrom exponent (SSAAE) becomes negative, indicating the presence of mineral dust (Collaud Cohen et al., 2004). Positive values are indicative SSAAE for aerosols optical properties dominated by combustion products.

Other mainly statistical methods were described by (Viana et al., 2010) based on chemical composition and positive matrix factorization source apportionment. Viana et al. compared two methods termed SPR and TAU. African dust episodes are detected with the SPR method at a given location by means of a combination of tools which include:
- back-trajectory analysis (NOAA-Hysplit http://ready.arl.noaa.gov/HYSPLIT-.php),
- satellite imagery (NASA-SeaWIFS http://oceancolor.gsfc.nasa.gov/SeaWiFS/), and
- aerosol dust maps (SKIRON http://forecast.uoa.gr/, BSC-DREAM http://www.bsc.es/projects/earthscience/DREAM/, NRL-NAAPS http://www.nrlmry.navy.mil/aerosol/).

According to this method, identification of episodic days is followed by discrimination of African dust (AD) from regional/local dust arising from dust resuspension processes, city dust, etc., and quantification of African dust. The daily regional background $PM_{10}$ level for days without AD is calculated as the 30 days moving 40th percentile for $PM_{10}$ levels at a regional background site (belonging or not to the EMEP network, European Monitoring and Evaluation Programme), after removal of the episodic days from the time series. Subsequently, the difference between the regional background level on days without AD, and on days with AD, is used to estimate the daily contribution of AD. This daily contribution of AD may then be subtracted from the daily PM levels at urban background locations.

On the other hand, the TAU method aims to identify and quantify AD using only hourly $PM_{10}$ measurements from automatic stations (Ganor et al, 2009; https://doi.org/10.1016/j.atmosenv.2009.07.028). The automatic algorithm uses three thresholds, whereby an episode is identified as an AD event only if the following apply: the half-hour $PM_{10}$ average is above 100 μg/m$^3$, this level is maintained for at least 3 h, and the maximum concentration recorded is above 180 μg/m$^3$. To quantify AD, the TAU method calculates the difference between the average $PM_{10}$ during a given period and the average $PM_{10}$ without AD contributions for that same period.

The approaches described in above mentioned methods differ from the present invention, as they are based on calculation of several different parameters, while the present invention uses measurements in two fractions of air to obtain one set of data, namely dust concentration in particular time points.

DESCRIPTION OF THE SOLUTION OF THE TECHNICAL PROBLEM

The aim of the present invention is to develop a quantitative method for determination of mineral dust in ambient aerosol. The method according to the invention is based on measurements of particle absorption as absorption gives much more specific results than scattering. However, the determination of the optical absorption of pure mineral dust, if or when mixed with black carbon, is more difficult because black carbon features a much higher mass absorption cross-section, obscuring the smaller contribution of dust to absorption. Therefore, the method employs a virtual impactor enriching the aerosol coarse fraction, and hence increasing the contribution of weakly absorbing dust, which has never been used or proposed for increasing the dust aerosol absorption relative to black carbon.

The virtual impactor is a device used to separate particles by size into two airstreams. The impaction surface is a virtual space of stagnant or slow-moving air. Large particles are captured in a collection probe. Usually, aerosol passes through an accelerating nozzle and is directed toward a collection probe or a connected instrument. At this point a major portion of the flow is diverted 90° away from the collection probe, where the particle-size separation takes place. Small particles with low inertia follow the flow streamlines and are carried away radially with the major flow. Large particles with greater inertia deviate from the flowlines and continue moving axially in their forward path down the collection probe with the minor flow. The virtual impactor concentrates coarse particles with the concentration efficiency (CE) increasing with particle size toward the theoretical limit defined by the flow ratio $F_{in}/F_{out}$, where $F_{in}$ is the total inlet sample flow of the virtual impactor and $F_{out}$ the minor sample flow of the Aethalometer or any other suitable absorption photometers, preferably filter based absorption photometers such as Aethalometer® produced by Magee Scientific, USA. Thus, for $PM_1$ particles, which are smaller than 1 μm, there is not much enhancement (CEPM1<1.2), which is important because this fraction contains most of black carbon. Mineral dust, on the other hand, occupies the coarse aerosol fraction (sizes between 2.5 and 10 μm), which is efficiently concentrated by the virtual impactor. Said high-volume virtual impactor inlet is coupled with an aerosol absorption monitor to measure the absorption of concentrated particles. At the same time $PM_1$ fraction has to be sampled by the same or a further aerosol absorption monitor, to gain absorption of the $PM_1$ fraction. Finally, the absorption of concentrated coarse particles is obtained by subtracting the absorption of the fine aerosol fraction from the absorption of the virtual impactor sample.

The essence of the method for quantification of ambient mineral dust concentration is in that in comprises the following steps:

Sampling air samples with particle size smaller than 1 μm ($PM_1$) and sampling air samples with particle size up to 10 μm;

Concentrating the samples with particle sizes up to 10 μm with a virtual impactor;

Measuring optical absorption of collected samples at least one wavelength from UV to IR wavelength range, preferably from 370 to 950 nm, most preferably at 370 nm;

Subtracting the optical absorption at least one selected wavelength, preferably at 370 nm, of the samples with particle size smaller than 1 μm from the absorption of the sample concentrated by the virtual impactor and dividing the obtained absorption with a calibration constant, which is preferably regression slope of the linear regression between absorption (y-axis) and mass concentration (x-axis) from chemical analysis of mineral dust particles.

Calibration constant can be derived by comparing absorption measurement and mineral dust concentration as determined using an alternative method (chemical analysis on filter samples or any other). It can be determined using a regression slope between absorption and mineral dust concentration or by calculating the average ratio between these quantities. Calibration constant could also be obtained in a different manner, for example by determining average concentration efficiency for particles with sizes between 1 and 10 μm and mass absorption cross section (MAC). However, dividing the calibration constant into several parameters causes complication of the method; hence the regression slope is the preferred choice. Said regression slope can be empirically determined based on measurements of calcium concentration in desert dust (determined using mass closure, PCA or PMF or any other suitable method). One possible calculation of mineral dust concentration at any time point is thus:

$$PP = \frac{b_{abs,VI-PM1}}{db_{abs}/dPP}$$

wherein PP represents concentration of mineral dust, $b_{abs,VI-PM1}$ represents absorption of coarse particles in the sample, while $db_{abs}/dPP$ represents the empirically obtained regression slope. The regression slope depends on the optical properties of the mineral dust. It varies between locations and is thus calculated for each location where the method according to the invention is used.

Sampling and measurements of particle absorption for different size fractions are performed by any suitable device known in the field of aerosol analysis, preferably with at least two Aethalometers® (Magee Scientific, USA) for detection of black carbon running in parallel, the Aethalometers having different inlets a $PM_1$ inlet, and a virtual impactor (VI). Optical absorption can be measured at any wavelength from UV to IR, preferably at wavelengths 370 nm. The average absorption spectrum for mineral dust shows increased absorption at shorter wavelengths, where the curve deviates most from the Angstrom exponent of 1. To obtain best discrimination between mineral dust and black carbon, measurements at 370 nm provide better results for the determination of mineral dust, especially where samples contain black carbon.

Because $PM_1$ absorption is dominated by black carbon, it is essential to compensate data for the filter loading effect (Drinovec et al., 2017). For the Aethalometer with $PM_1$ inlet the data is sufficiently compensated by the built in dual-spot algorithm. For the Aethalometer connected to the virtual impactor, the algorithm was hindered by coarse particles. The main problem lies in the fact that a single particle (deposited on one of the two spots) potentially causes significant absorption only in one of the two measurement spots. This requires an application of off-line compensation using fixed values of the compensation parameters, wherein the loading effect is preferably characterized using the BC vs. ATN method (Park et al., 2010; Drinovec et al., 2015) the relevant equation being:

$$cBC = BC/(1 - k*ATN),$$

where cBC represents a black carbon concentration compensated for the filter loading effect, BC represents non-compensated black carbon concentration, k represents a compensation parameter and ATN represents optical attenuation of the particle laden filter. The compensation type depends on the type of the used photometer. The above equation is best suited for Aethalometer AE33. Other filter photometers need different type of compensation.

The mineral dust concentration data may be calculated at any time, at any time point or sequence of time points, preferably calculations are done with 1 minute or 1 hour time resolution to follow fast variations in airborne dust concentration and not only daily changes as with the 24 hour filter method.

The described method can be performed by the device for sampling and measuring absorbance, however the preferred choice for performing calculations based on measured absorbance is a computer connected to the measuring devices running a special software, by a computer program installed on a server or cloud, or any other suitable device. The device for performing the said method may be any suitable for executing described steps, the device preferably comprising at least two devices for sampling airborne particles and measurement of optical absorbance at any wavelength from UV to IR range, preferably from 370 nm to 950 nm, most preferably at 370 nm, and a computer for calculation of mineral dust concentration in any time point or sequence of time points, preferably with a one minute time resolution. The computer software performs the following calculations:

filter loading compensation of the AE33 data;
calculation of the coarse particle absorption by subtracting PM1 absorption from VI enhanced absorption; and
calculating a mineral dust concentration by dividing coarse particle absorption by the calibration constant.

Embodiment 1

The method is preferably performed by two Aethalometers model AE33 (Magee Scientific, USA) running in parallel and having different inlets—a BGI Inc. SCC 1.197 $PM_1$ sharp-cut cyclone ($PM_1$ inlet) and a virtual impactor (VI) as described above. The first instrument was sampling at a 5 l/min flow rate, while the one sampling through the VI was set at a 2 l/min flow rate in order to increase concentration efficiency of the VI. Other possible flows are from 1 to 5 l/min, preferably 2 l/min. The virtual impactor (VI) samples from 50 to 120 l/min, preferably 100 l/min of ambient air. The majority of the air is carried out of the VI by a large capacity pump. The coarse particles are inertially "impacted" into the minor flow, carried by the exhaust tube to the connected instrument. Sample flow must be larger than minor flow, wherein the exact values of the minor and the sample flow depend on the design of the virtual impactor. In general larger ratio of sample flow/minor flow results in higher concentration efficiency. For the experimental setup in embodiment 1 the highest concentration efficiency was obtained by using the minor flow of 2 l/min and sample flow of 100 l/mim. Optical absorption measurements by the Aethalometers are performed at 370 nm. Optical absorption of the coarse fraction of mineral dust was determined by subtracting optical absorption of sub 1 μm fraction from the absorption of all particles concentrated by the virtual impactor and the concentration of mineral dust particles in air was determined with the equation:

$$C(dust) = b\_abs(VI-PM1)/RS,$$

wherein the regression slope RS was the regression slope of the linear regression between absorption (y-axis) and mass concentration (x-axis) from calcium concentration in desert dust and the filter loading effect was compensated as described above.

The method and the device according to the invention, enable following of mineral dust occurrence in real-time as well as reliable quantification of mineral dust in air to allow correction of days on which the PM value was exceeded, while at the same time ensuring simplicity of measurement and result interpretation due to one parameter calculation.

The invention claimed is:
1. A method for quantification of ambient mineral dust concentration, said method comprising the following steps:
sampling air samples with particle size smaller than 1 μm ($PM_1$) and sampling air samples with particle size up to 10 μm;
concentrating the air samples with particle sizes up to 10 μm with a virtual impactor (VI);
measuring optical absorption of the sampled air samples at at least one wavelength from 370 to 950 nm;
subtracting the absorption at the at least one wavelength from 370 to 950 nm, of the air samples with particle size smaller than 1 μm from the absorption of the sample concentrated by the virtual impactor and dividing a difference result of the subtraction with a calibration constant.
2. The method according to claim 1, wherein the calibration constant is a regression slope of the linear regression between absorption on y-axis and mass concentration on x-axis from chemical analysis of mineral dust particles.
3. The method according to claim 2, wherein mass concentration on x-axis from chemical analysis of mineral dust particles is based on measurements of calcium concentration using mass closure, principal component analysis (PCA) or positive matrix factorization (PMF).

4. The method according to claim 1, wherein the calibration constant is obtained by determining average concentration efficiency for particles with sizes between 1 and 10 µm and mass absorption cross section (MAC).

5. The method according to claim 2, wherein the calculation of mineral dust concentration at any time point is:

$$PP = \frac{b_{abs,VI-PM1}}{db_{abs}/dPP}$$

wherein PP represents concentration of mineral dust, $b_{abs,\ VI-PM1}$ represents absorption of coarse particles in the sampled air samples, while $db_{abs}/dPP$ represents the empirically obtained regression slope.

6. The method according to claim 1, wherein the optical absorption is measured at least one wavelength from UV to IR wavelength range, from 370 to 950 nm.

7. The method according to claim 1, wherein sampling and measurements of particle absorption for different size fractions are performed by any suitable absorption photometer, with at least two Aethalometers for detection of black carbon running in parallel, said Aethalometers having a $PM_1$ inlet and a VI inlet.

8. The method according to claim 1, wherein data for a filter loading effect are compensated with an off-line compensation using equation cBC=BC/(1-k*ATN), where cBC represents a black carbon concentration compensated for the filter loading effect, BC represents non-compensated black carbon concentration, k represents a compensation parameter and ATN represents optical attenuation of a particle laden filter.

9. The method according to claim 1, wherein mineral dust concentration data is calculated at any time point or sequence of time points.

10. The method according to claim 1, where it wherein the method is performed by a device for sampling and measuring absorbance or by a computer running a suitable software connected to measuring devices, by suitable software installed on a server or cloud.

11. The method according to claim 10, wherein the software performs at least the following calculations:
    filter loading compensation of aethalometer data;
    calculation of a coarse particle absorption by subtracting the absorption of PM1 from the absorption of the particles from the VI; and
    calculation of mineral dust concentration by dividing coarse particle absorption by the calibration constant.

12. A device performing the method according to claim 1, wherein the device comprises at least two devices for sampling airborne particles and measurement of optical absorbance at any wavelength from 370 nm to 950 nm, and a computer for calculation of mineral dust concentration in any time point or sequence of time points.

* * * * *